US008070139B2

(12) United States Patent
Nassirpour et al.

(10) Patent No.: US 8,070,139 B2
(45) Date of Patent: Dec. 6, 2011

(54) AIR TREATMENT DEVICE HAVING AN AUDIBLE INDICATOR

(75) Inventors: Sanam Nassirpour, Phoenix, AZ (US); Jeffrey Bankers, Phoenix, AZ (US); Jeff Gaunt, Phoenix, AZ (US)

(73) Assignee: The Dial Corporation, Scottsdale, AZ (US)

( * ) Notice: Subject to any disclaimer, the term of this patent is extended or adjusted under 35 U.S.C. 154(b) by 420 days.

(21) Appl. No.: 12/351,404

(22) Filed: Jan. 9, 2009

(65) Prior Publication Data
US 2009/0185958 A1 Jul. 23, 2009

Related U.S. Application Data

(60) Provisional application No. 61/020,588, filed on Jan. 11, 2008.

(51) Int. Cl.
*A61L 9/12* (2006.01)
*B01F 3/04* (2006.01)

(52) U.S. Cl. .............. 261/30; 55/DIG. 34; 55/385.1; 96/22; 96/419; 239/34; 239/42; 239/211; 422/105; 422/123; 261/DIG. 65; 261/DIG. 88

(58) Field of Classification Search ........... 55/385.1, 55/DIG. 34; 96/22, 419; 239/34, 42, 211; 422/105, 123; 261/30, DIG. 65, DIG. 88
See application file for complete search history.

(56) References Cited

U.S. PATENT DOCUMENTS

| 4,889,284 | A * | 12/1989 | Spector | 239/34 |
| 5,590,696 | A * | 1/1997 | Phillips et al. | 141/47 |
| 6,708,692 | B2 * | 3/2004 | Lee et al. | 128/205.24 |
| 7,108,199 | B1 * | 9/2006 | Brown | 239/70 |
| 2005/0072855 | A1 * | 4/2005 | Brown | 239/34 |
| 2006/0261179 | A1 * | 11/2006 | Davies et al. | 239/34 |
| 2007/0095941 | A1 * | 5/2007 | Gorres | 239/337 |
| 2008/0156896 | A1 * | 7/2008 | Anderson et al. | 239/34 |
| 2008/0237248 | A1 * | 10/2008 | Dente et al. | 220/729 |

* cited by examiner

*Primary Examiner* — Robert A Hopkins
*Assistant Examiner* — Minh-Chau Pham
(74) *Attorney, Agent, or Firm* — Snell & Wilmer L.L.P.

(57) ABSTRACT

The present invention provides a system for dispensing an air treatment and audibly indicating the dispensing and/or a change in the dispensing intensity. An exemplary audible indicator may include a pattern of a plurality of audible indicators having the same or different durations, having the same or different intensities, separated by the same or different intervals, and having the same or different audible impressions. Different audible indicators are associated with different device states, such as not dispensing, dispensing to create ambiance, dispensing in response to a malodor, or dispensing to offset habituation. Different audible indicators may also be associated with different malodors, or different intensities of the same or different malodors.

22 Claims, 2 Drawing Sheets a) ---------------- b) ----  ----  ---- c) ---  --  ---  -- d) -  --  ---  ----  ----- e) ----  -----  ----- f) ----  ---  ----  --- g) -  --  ---  ----  ----- h) ----  -----  ----- i) ----  ---  ----  --- j) -  --  ---  ----  ----- k) ----  *****  ---- l) ----    ---- m) - // *** >>>> @@@@@

FIG. 1

AIR TREATMENT DEVICE HAVING AN AUDIBLE INDICATOR

CROSS-REFERENCE TO RELATED APPLICATIONS

This U.S. Non-Provisional patent application claims priority to U.S. Provisional Patent Application Ser. No. 61/020,588 entitled "AIR TREATMENT DEVICE HAVING AN AUDIBLE INDICATOR" and filed on Jan. 11, 2008.

FIELD OF INVENTION

The present invention generally relates to vapor-dispensing devices. More particularly, the system may include an audible indicator.

BACKGROUND OF THE INVENTION

Vapor-dispensing devices typically include a volatizable material and a dispensing system configured to facilitate evaporation of the volatizable material into the surrounding air. For example, in some systems, a liquid material is contained in a reservoir, and is volatized with heat, pump, aerosol, fan, etc.

Known vapor-dispensing devices may be improved upon in a number of respects. For example, a consumer may wish to be notified of an air treatment to appreciate its effectiveness.

SUMMARY OF THE INVENTION

The present invention provides a system for dispensing an air treatment and audibly indicating the dispensing and/or a change in the dispensing intensity.

An exemplary audible indicator is the "hiss" sound commonly associated with known pump and aerosol dispensing systems. An exemplary audible indicator may comprise a pattern of a plurality of audible indicators having the same or different durations, having the same or different intensities, separated by the same or different intervals, and having the same or different audible impressions.

In an exemplary embodiment, different audible indicators are associated with different device states, such as not dispensing, dispensing to create ambiance, dispensing in response to a malodor, or dispensing to offset habituation. In another exemplary embodiment, different audible indicators are associated with different malodors, or different intensities of the same or different malodors. In yet other exemplary embodiments, different audible indicators are associated with different volatizable materials to be evaporated into the surrounding air or the remaining amount of volatizable material to be evaporated into the surrounding air.

The present invention also provides a system for visual indications similar to the audible indications described herein.

By providing a user with an audible and/or a visual indicator, a user is notified and need not "trust" or merely assume that the vapor-dispensing device is functioning properly.

BRIEF DESCRIPTION OF THE DRAWINGS

FIG. 1 illustrates exemplary audible indicator patterns.

DETAILED DESCRIPTION

Figure 2:
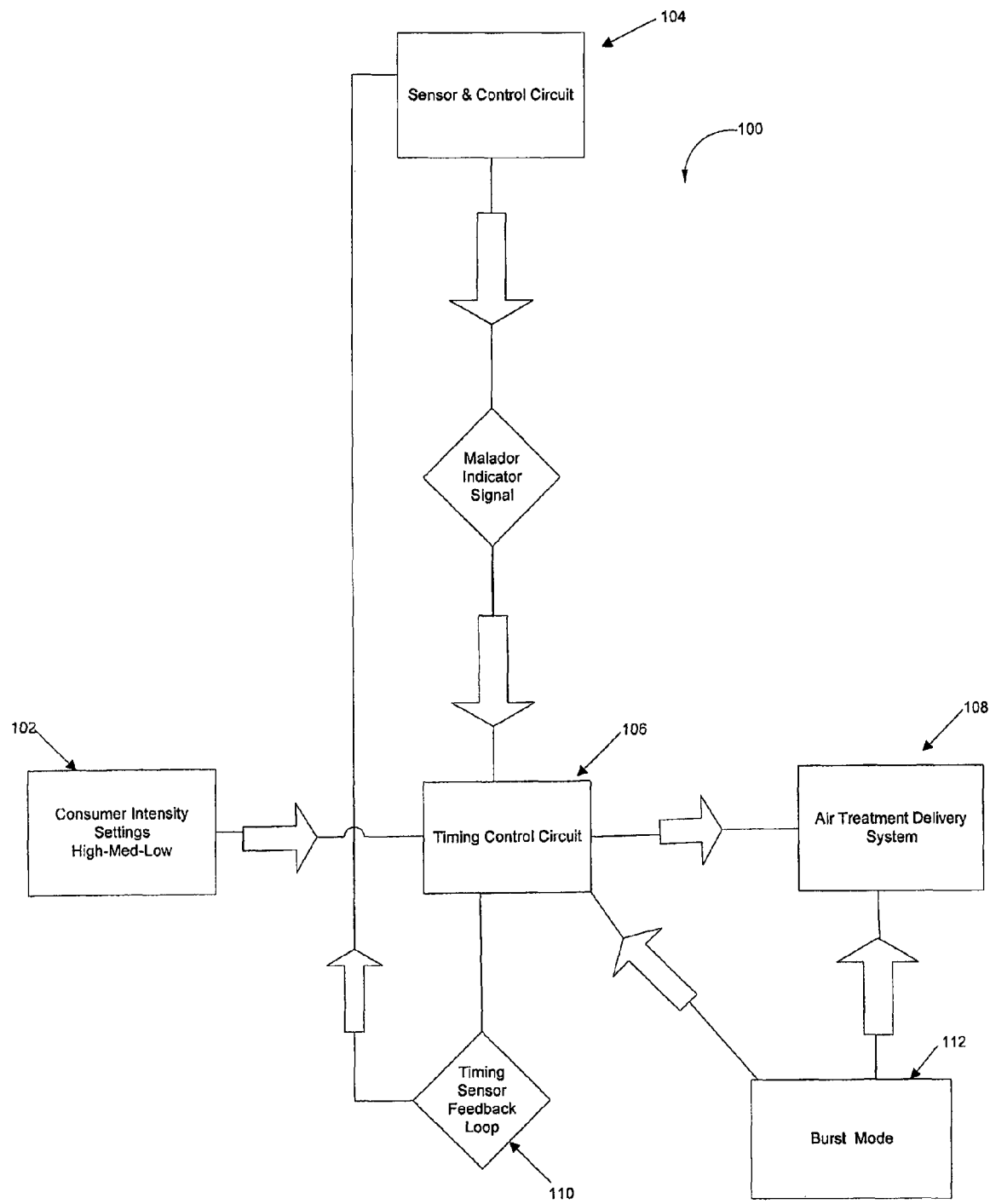
FIG. 2 shows a block diagram of a method and system of an exemplary air treatment device.

The following descriptions are of exemplary embodiments of the invention only, and are not intended to limit the scope or applicability of the invention in any way. Rather, the following description is intended to provide convenient illustrations for implementing various embodiments of the invention. As will become apparent, various changes may be made without departing from the spirit and scope of the invention as set forth in the appended claims.

For the sake of brevity, functional embodiments of the apparatus and systems (and components of the individual operating components of the systems) may not be described in detail herein. Furthermore, the connecting lines shown in the various figures contained herein are intended to represent exemplary functional relationships and/or physical connections between the various elements. It should be noted that many alternative or additional functional relationships or physical connections may be present in a practical system.

The present invention provides a system for dispensing an air treatment comprising a volatizable material and a dispensing system configured to facilitate evaporation of the volatizable material into the surrounding air and audibly indicate to a user the dispensing, a change in the dispensing intensity and/or a change in the nature or character of the dispensing.

An audible indicator can be any audible cue generally discernable by a user. An exemplary audible indicator is the "hiss" sound commonly associated with known pump and aerosol dispensing systems. Other exemplary audible indicators include snaps, beeps, and other onomatopoeias, and voice, music, and sound effects. In general, any audible cue capable of notifying a user of the dispensing and/or a change in the dispensing is appropriate for use herein.

Figure 1:
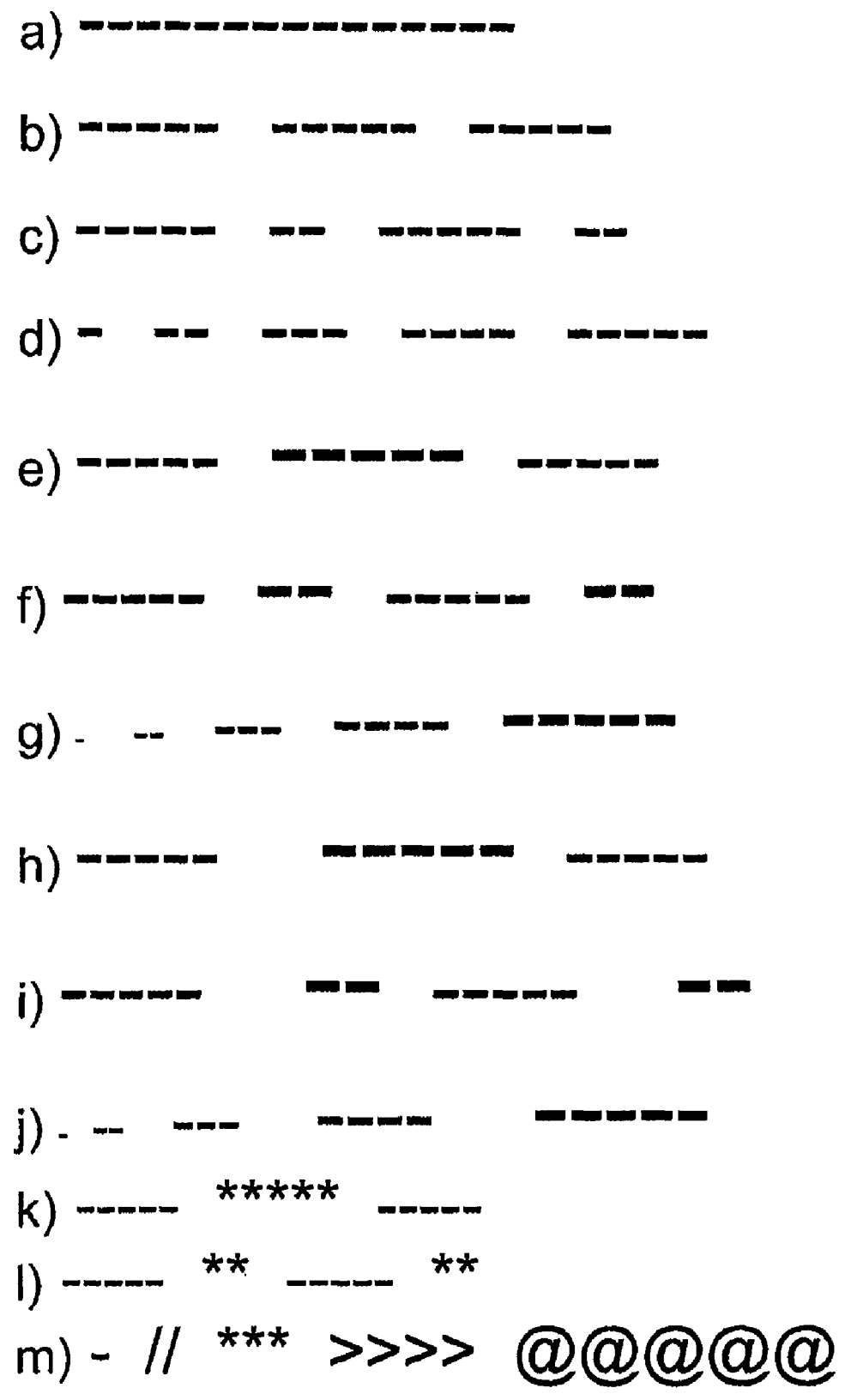

As shown in FIG. 1, an exemplary audible indicator may comprise a pattern of a plurality of audible indicators having the same or different durations, such as patterns b-d in FIG. 1. The different durations are relative to each other and generally discernable by a user. For example, a duration of an audible indicator may be temporally shorter, the same as, or longer, relative to another. The durations may be any suitable amount of time, for example, 1 millisecond, 5 milliseconds, 10 milliseconds, up to several seconds or more, and need not be the same as another or follow a pattern or trend.

A plurality of audible indicators may have the same or different intensities and/or volumes, such as patterns e-g in FIG. 1. The different intensities are relative to each other and generally discernable by a user. For example, an intensity may be less than, the same as, or greater than another.

Additionally, a plurality of audible indicators may be separated by the same or different intervals, such as patterns h-j in FIG. 1. The different intervals are relative to each other and generally discernable by a user. For example, an interval between audible indicators may be temporally shorter, the same as, or longer, relative to another. The intervals may be any suitable amount of time, for example, 1 millisecond, 5 milliseconds, 10 milliseconds, up to several seconds or more, and need not be the same as another or follow a pattern or trend.

A plurality of audible indicators may also have the same or different audible impressions, such as patterns k-m in FIG. 1. The different audible impressions are relative to each other and generally discernable by a user. For example, a first audible impression might be a "hiss" sound and a second audible impression might be a "snap" sound.

In an exemplary embodiment, different audible indicators are associated with different device states, such as dispensing to create ambiance, dispensing in response to a malodor, or dispensing to offset habituation. For example, a consumer may wish to know when a vapor-dispensing device is operating at a normal level to create ambiance and when it is operating at an elevated level in response to a malodor or to offset habituation. In an exemplary embodiment, dispensing to create ambiance, dispensing in response to a malodor, and dispensing to offset habituation are each characterized by different audible indicators.

In another exemplary embodiment, different audible indicators are associated with different malodors, or different intensities of the same or different malodors. In this regard, the present invention provides a sensory mechanism which, upon sensing of a certain malodor, directs the device to dispense a volatizable material and notifies the consumer by an audible cue what the vapor-dispensing device is responding to. For example, dispensing in response to a low level of kitchen smoke might produce a first sound, dispensing in response to a high level of kitchen smoke might produce a second sound, and dispensing in response to an onion might produce a third sound.

In yet another exemplary embodiment, different audible indicators are associated with different volatizable materials to be evaporated into the surrounding air. For example, dispensing a first volatizable material may be associated with a first audible indicator, and dispensing a second volatizable material may be associated with a second audible indicator. In this manner, a consumer is notified by an audible cue what is being evaporated into the surrounding air.

In yet another exemplary embodiment, different audible indicators are associated with the remaining amount of volatizable material to be evaporated into the surrounding air. For example, a first remaining amount of volatizable material may be associated with a first audible indicator, and a second remaining amount of volatizable material may be associated with a second audible indicator. In this manner, a consumer is notified by an audible cue how much volatizable material remains.

The present invention also provides a system for dispensing an air treatment and visually indicating the dispensing and/or a change in the dispensing intensity.

An exemplary visual indicator is an LED or LCD. An exemplary visual indicator may comprise a pattern of a plurality of visual indicators having the same or different durations, having the same or different intensities, separated by the same or different intervals, and having the same or different visual impressions.

In an exemplary embodiment, different visual indicators are associated with different device states, such as dispensing to create ambiance, dispensing in response to a malodor, or dispensing to offset habituation. In another exemplary embodiment, different visual indicators are associated with different malodors, or different intensities of the same or different malodors. In yet other exemplary embodiments, different visual indicators are associated with different volatizable materials to be evaporated into the surrounding air or the remaining amount of volatizable material to be evaporated into the surrounding air.

Either audible or visual indicators may be used alone or in combination with the other.

As an example, in accordance with various embodiments of the present invention, activation or operation of an air treatment device depends on the consumer's desired interaction (or lack thereof). Specifically, in certain instances a consumer may wish to have a sensor activated treatment, e.g., the air treatment device is automatically activated in response to a malodor, for example, to conserve volatizable material and/or power. In other instances a consumer may wish to have a timed treatment, e.g., the air treatment device is active at certain times or for certain periods. Still further, a consumer may wish to have both a sensor activated treatment and a timed treatment. In one embodiment, the present invention provides a method and system for dispensing an air treatment and audibly notifying a consumer of the dispensing.

A method and system are described below wherein the combination of the consumer's interaction (or lack thereof), the sensor activated treatment of the air, and the timed treatment of the air, are interdependent. In an exemplary embodiment shown in FIG. 2, the air treatment system 100 includes a dispensing system 108, a selection mechanism 102, a sensor 104, and a timing control circuit 106.

Dispensing system 108 expels the air treatment material when a malodor is detected by sensor 104 or in accordance with a timed treatment. In some embodiments, timing control circuit 106 causes dispensing system 108 to disperse the air treatment. Dispensing system 108 can be any system capable of dispensing the air treatment material as appreciated by one of ordinary skill in the art.

A consumer may wish to be notified of an air treatment to appreciate its effectiveness. The present invention provides a system for dispensing an air treatment when needed and audibly notifying a consumer of the dispensing. FIG. 1 illustrates exemplary audible spraying patterns. An exemplary audible spraying pattern may comprise one or more sprays of the same or different durations and/or intensities, separated by the same or different intervals. In an exemplary embodiment, variable durations, intensities, and/or intervals are controlled by timing control circuit 106 or a spraying pattern control module (not shown).

The entire duration of an exemplary audible spraying pattern may be any time suitable to notify a consumer of the dispensing. In exemplary embodiments, the entire duration of an exemplary audible spraying pattern is from about 50 milliseconds to about 10 seconds. It should be appreciated however, that the entire duration may be shorter than 50 milliseconds or significantly longer than 10 seconds.

In accordance with some embodiments, spraying patterns may be different depending on whether the treatment is a sensing treatment or a timed treatment. In accordance with other embodiments, spraying patterns may be different depending on the particular malodor the air treatment device is responding to. In accordance with other embodiments, spraying patterns may be different depending on the particular timed treatment, e.g., the start time of the treatment, the duration of the treatment, or the intervening time between treatments.

In accordance with yet other embodiments, spraying patterns may be supplemented with other audio or visual indicators. For example, spraying patterns may be supplemented with sound effects or light effects at variable durations, intensities, and/or intervals.

Turning back to FIG. 2, in an exemplary embodiment, selection mechanism 102 operates to indicate in what audible spraying pattern the air treatment system will operate. In another exemplary embodiment, selection mechanism 102 operates to indicate in what mode the air treatment system will operate. Selection mechanism 102 may be set for a sensing treatment, a timed treatment, or a combination thereof. In such embodiments, each of the sensing and timed treatment may be adjusted to high, medium, low, and off, depending on the desired level of treatment required by the consumer. Selection mechanism 102 communicates with timing control circuit 106 to help assure the consumer's desired level of treatment. Selection mechanism 102 may be a switch or any other suitable mechanism that allows the consumer to indicate in what mode the air treatment system will operate.

Sensor 104 samples the environment for either the level of air treatment material or the quality of the current environment. In one exemplary embodiment, sensor 104 is capable of detecting a malodor. In another exemplary embodiment, sensor 104 is capable of distinguishing between a plurality of malodors in a plurality of locations such that a single air treatment system 100 may be used in multiple locations. In yet another exemplary embodiment, a consumer may wish to have a sensor activated or deactivated air treatment device, for example, for conservation of power. An aspect in accordance with various embodiments of the foregoing invention, is sensor 104 being capable of detecting a plurality of environmental conditions, for example, light, sound and/or motion. In general, any suitable sensor exhibiting the qualities discussed herein may be used in the context of the present invention.

Timing control circuit 106 activates air treatment system 100 and causes dispensing system 108 to disperse the air treatment material at certain times or for certain periods. Timing control circuit 106 allows for a sensing treatment, a timed treatment, or a combination thereof.

For the sensing treatment, timing control circuit 106 and sensor 104 are interconnected by a feedback circuit 110 such that sensor 104 controls timing control circuit 106 and vice-versa. Thus, sensor 104 controls timing control circuit 106 in that, when sensor 104 detects a malodor, an indication signal is sent to timing control circuit 106. Timing control circuit 106 will then cause dispensing system 108 to disperse the air treatment. In an exemplary embodiment, timing control circuit 106 further disengages sensor 104 for an operational time period via feedback circuit 110 if timing control circuit 106 causes a certain period of increased air treatment.

Among other advantages, in some embodiments, the interconnection of timing control circuit 106 and sensor 104 by feedback circuit 110 provides for power conservation. Specifically, because in some embodiments sensor 104 may need to be heated to a high temperature to work (e.g. metal oxide sensors), there is power conservation if timing control circuit 106 also controls sensor 104. For example, timing control circuit 106 can deactivate sensor 104 when it is not in use.

For the timed treatment, air treatment system 100 is activated in a timed manner that is controlled in terms of one or more of the start time of the treatment, the duration of the treatment, commonly referred to as "on time," and the intervening time between treatments, commonly referred to as "off time." In an exemplary embodiment, timing control circuit 106 contains interval timed programming wherein air treatment material is dispersed in predetermined intervals during the "on time." Timing control circuit 106 will then cause dispensing system 108 to disperse the air treatment.

Another aspect in accordance with various embodiments of the invention is the burst mode 112. Burst mode 112 may be initiated by an actuator on the device to dispense the air treatment material. In an exemplary embodiment, burst mode 112 would communicate with timing control circuit 106, which would then activate dispensing system 108 to relatively immediately dispense the air treatment material. A user may actuate a button or another indication may be provided, which would signal that dispensing of the air treatment material is desired. In another exemplary embodiment, burst mode 112 would directly activate dispensing system 108 to dispense the air treatment material. This feature may further provide an air treatment to mask, neutralize and/or otherwise remove malodors within the area. Burst mode 112 may function alone or in combination with either or both of a sensing treatment and a timed treatment.

It should be understood that the foregoing description is of exemplary embodiments of the invention only, and that the invention is not limited to the specific forms shown. Various modifications may be made in the design and arrangement of the elements set forth herein without departing from the scope of the invention.

What is claimed is:

1. An air treatment device for dispensing a volatizable material comprising:
   a volatizable material;
   a dispensing system; and
   a reservoir in communication with said volatizable material and said dispensing system;
   wherein said dispensing system is configured to produce an audible indicator upon said dispensing system dispensing a volatizable material, wherein the audible indicator indicates a change in the dispensing intensity level.

2. A device as in claim 1, wherein said audible indicator comprises an onomatopoeia.

3. A device as in claim 2, wherein said onomatopoeia is a "hiss" sound.

4. A device as in claim 1, wherein said audible indicator lasts from about 1 millisecond to about 3 seconds.

5. A device as in claim 1, wherein said audible indicator is an audible indicator pattern comprising a plurality of said audible indicators that include one or more of:
   same or different durations;
   same or different intensities;
   same or different intervals of separation; and
   same or different audible impressions.

6. An air treatment device for dispensing a volatizable material comprising:
   a first volatizable material;
   a dispensing system; and
   a reservoir in communication with said volatizable material and said dispensing system;
   wherein said dispensing system is configured to produce a first predetermined audible indicator and a second predetermined audible indicator.

7. A device as in claim 6, wherein at least one of said first and second audible indicators comprises an onomatopoeia.

8. A device as in claim 6, wherein said first audible indicator is produced upon said device being in a first state, and said second audible indicator is produced upon said device being in a second state.

9. A device as in claim 8, wherein said first state is one of:
   not dispensing;
   dispensing to create ambiance;
   dispensing in response to a malodor; and
   dispensing to offset habituation.

10. A device as in claim 9, wherein said second state is one of:
    not dispensing;
    dispensing to create ambiance;
    dispensing in response to a malodor; and
    dispensing to offset habituation.

11. A device as in claim 10, wherein at least one of said first and second audible indicators is an audible indicator pattern comprising a plurality of said audible indicators.

12. A device as in claim 6, wherein said first audible indicator is produced upon dispensing in response to a first malodor, and said second audible indicator is produced upon dispensing in response to a second malodor.

13. A device as in claim 12, wherein at least one of said first and second audible indicators is an audible indicator pattern comprising a plurality of said audible indicators.

14. A device as in claim 6, wherein said first audible indicator is produced upon dispensing in response to a malodor in a first intensity, and said second audible indicator is produced upon dispensing in response to said malodor in a second intensity.

15. A device as in claim 6, wherein at least one of said first and second audible indicators is an audible indicator pattern comprising a plurality of said audible indicators.

16. A device as in claim 6, further comprising a second volatizable material, wherein said first audible indicator is produced upon dispensing said first volatizable material, and said second audible indicator is produced upon dispensing said second volatizable material.

17. A device as in claim 16, wherein at least one of said first and second audible indicators is an audible indicator pattern comprising a plurality of said audible indicators.

18. A device as in claim 6, wherein said first audible indicator is produced upon there remaining a first amount of said volatizable material, and said second audible indicator is produced upon there remaining a second amount of said volatizable material.

19. A device as in claim 18, wherein at least one of said first and second audible indicators is an audible indicator pattern comprising a plurality of said audible indicators.

20. A method for audibly notifying a user of a volatizable material being dispensed comprising dispensing a volatizable material and producing an audible indicator upon said dispensing, wherein said audible indicator is an audible indicator pattern comprising a plurality of said audible indicators that include one or more of:
    same or different durations;
    same or different intensities;
    same or different intervals of separation; and
    same or different audible impressions.

21. A method for dispensing a volatizable material comprising automatically detecting a first state, producing a first predetermined audible indicator upon detecting said first state, automatically detecting a second state, and producing a second predetermined audible indicator upon detecting said second state, wherein said first and second states are each one of not dispensing;
    dispensing to create ambiance;
    dispensing in response to a malodor; and
    dispensing to offset habituation.

22. An air treatment device for dispensing a volatizable material comprising:
    a volatizable material;
    a dispensing system; and
    a reservoir in communication with said volatizable material and said dispensing system;
    wherein said dispensing system is configured to produce a visual indicator upon said dispensing system dispensing a volatizable material, wherein the visual indicator indicates a change in the dispensing intensity level, and
    wherein said visual indicator is a visual indicator pattern comprising a plurality of said visible indicators that include one or more of:
    same or different durations;
    same or different intensities;
    same or different intervals of separation; and
    same or different visual impressions.

\* \* \* \* \*